(12) United States Patent
Griffin

(10) Patent No.: US 6,246,817 B1
(45) Date of Patent: Jun. 12, 2001

(54) OPTICAL FIBER WITH NUMERICAL APERTURE COMPRESSION

(75) Inventor: Stephen Griffin, Phoenix, AZ (US)

(73) Assignee: Innova Quartz Inc., Phoenix, AZ (US)

( * ) Notice: Subject to any disclaimer, the term of this patent is extended or adjusted under 35 U.S.C. 154(b) by 0 days.

(21) Appl. No.: 09/144,920

(22) Filed: Sep. 1, 1998

(51) Int. Cl.$^7$ ........................... G02B 6/26
(52) U.S. Cl. ........................... 385/43
(58) Field of Search ........................... 385/43, 39, 33, 385/115, 116

(56) References Cited

U.S. PATENT DOCUMENTS

| | | | |
|---|---|---|---|
| 5,058,978 | * 10/1991 | Kondoh et al. | |
| 5,133,709 | * 7/1992 | Prince | |
| 5,512,078 | 4/1996 | Griffin | |
| 5,562,657 | 10/1996 | Griffin | |
| 5,852,692 | * 12/1998 | Nightingale et al. | |

OTHER PUBLICATIONS

IEEE Photonics Tech. Letters, vol. 6, No. 7, Jul. 1994 Fabrication of Expanded Core Fiber . . . .
SPIE–Proceedings of $6^{Th}$ Meeting in Israel on Optical Engineering, 1988 "Optical Fiber Up–Tapers . . . ".
Journal of Lightwave Technology, vol. LT5#8, Aug. 1987 Optical Fibers at 1.3 $\mu$m.
IEEE, vol. 8, No. 8, Aug. 1990, Beam Expending Fiber Using Thermal Diffusion . . . .
IEEE, vol. 4, No. 12, Dec. 1992, Loss Characteristics of Thermally Diffused . . . .
SPIE, vol. 1504, Fiber Optic Metrology & Standards, 1991 Novel Applications of Monomode Fibre Tapers.
IEEE, vol. 14, No. 10, Oct. 1996—Characteristics of Thermally Expanded Code Fiber.
Journal of Lightwave Tech., vol. LT–5, No. 1, Jan. 1987 Optical Fiber Tapers . . . .

* cited by examiner

Primary Examiner—Frank G. Font
Assistant Examiner—Tu T. Nguyen
(74) Attorney, Agent, or Firm—The Halvorson Law Firm

(57) ABSTRACT

A fiber optic probe of the type typically used in medical instruments includes an illumination optical fiber having a relatively high Numerical Aperture (NA) for coupling as much light as possible into the fiber at its input end. At the output end, an outwardly flared uniform taper is provided to increase collimation of the light exiting from the illumination end, thereby causing the Numerical Aperture (NA) at the output end of the illumination fiber to be a lower NA than that at the input end. For optical spectroscopy applications, collection fibers are located in close proximity to or surrounding the tapered output end of the illumination fiber for collecting reflected or scattered light rays from a target for use in qualitative and quantitative analysis of material.

34 Claims, 3 Drawing Sheets

OPTICAL FIBER WITH NUMERICAL APERTURE COMPRESSION

BACKGROUND

In the fields of spectroscopy and surgery, optical fibers employing laser inputs are increasingly being used. For surgery, optical fibers are often used in illumination of body cavities, imaging those cavities and in delivering laser energy for incision/excision, coagulation, homeostasis, and vaporization of tissue. Typically, the optical fibers which are used require a relatively high Numerical Aperture (NA) in order to capture as high a percentage as possible of the optical energy available from the laser source. High NA fibers, however, result in relatively wide divergence of the light spots at a relatively short distance from the ends of the fibers. Such divergence is not permissible for many applications; so that relatively expensive and cumbersome lens systems have been attached to the output ends of such fibers in order to focus or collimate (or nearly collimate) the light exiting from the output end of the fiber. Such lenses must be added to the fiber end as a separate manufacturing step, and tend to cause the endoscope (or spectroscopic probe tip) to be larger and more invasive than would be the case if such lens systems were not required.

Surgical fibers for energy delivery often are damaged in use, due to inadvertent contact with the target tissues. Contamination of the fiber output with tissue causes localized heating and consequent damage to the fiber, reducing the output beam quality. The wide-angle divergence of energy from high NA fibers contributes to this failure, in that the surgeon, in his search for the energy density he desires for the sought tissue effects, often inadvertently overshoots. This results from the fact that the high energy densities are found only very close to the fiber output; so unintended fiber/tissue contact is likely.

With lower NA output of a fiber, energy densities do not fall off as quickly; so that fiber/tissue separation of greater distances can be attained. Lower NA fibers are often incompatible with the launch NA of laser sources (and other, e.g. white light sources) used. A common additional problem is the minimum focal spot size of sources being larger than the optimum fiber core diameter. Typically, tapered fibers are used where the desired fiber is smaller than the minimal launch focal spot. While inefficient (typically 65%), these arrangements are often acceptable in many applications.

A popular pulsed Holmium doped yttrium-aluminum Garnet crystal laser (Ho:YAG), used in laser lithotripsy has a minimum focal spot size of approximately 300 $\mu$M diameter. 300 $\mu$M core fiber, however, is often too stiff to reach easily through small, highly twisted lumen of the type encountered in a human ureter, the location of the calcium carbonate kidney stones that lithotripsy is designed to treat. The maximum power of the laser, however, exceeds the minimum energy required to break up the stones; so that a surgeon is content with inefficient delivery if some means can be devised to get at least some significant portion of the laser energy into a smaller core fiber. It is desirable to use a smaller core fiber in order to achieve the flexibility not attainable with a 300 $\mu$M core diameter.

Other applications, such as assemblies for performing diagnostics, for example, identification of cancerous versus non-cancerous tissues by Raman spectroscopy also are increasingly utilized. In spectroscopy, several basic configurations exist with applications in absorption/transmission, and fluorescence (including phosphorescence and Raman spectroscopy). A single fiber may be used to deliver and collect reflected or scattered energy when external optics are used to split the signal return and the excitation signal.

The basic fiber configuration typically includes a relatively high NA excitation fiber, which is uniform throughout its length. The path length for the absorption spectroscopy measurement then is determined by mounting the fiber in a threaded carrier tube, with a mirror on an attaching cap spaced a distance one-half that of the desired path (due to the reflection of the mirror causing the light to transverse the space twice). Ideally, collimated or nearly collimated light (consistent with low NA fiber) is desired from the exit end of the excitation fiber; so that a maximum return of light is available for the return path. However, this is inconsistent with high NA fibers designed to capture the maximum light energy available from the source.

In spectroscopy, dual fiber devices or multiple fiber devices also may be employed, with one fiber being used as the excitation or illumination fiber and the others arranged in close proximity or surrounding the excitation fiber comprising the detection or collection fibers. Many of the same problems which exist with surgical applications also apply to these fiber optic spectroscopy devices. At the output end of the excitation fiber, it is desirable to have the light exit in a collimated or near collimated form. For high NA fibers, however, a relatively wide angle of light rays exit the end of the fiber; so that there is a relatively large circle of light or scattering at a relatively short distance from the fiber end. To overcome this, separate-lens systems may be applied to the end of the fiber. These lens systems present additional complications in spectral performance in addition to those previously noted.

It is desirable to provide an optical fiber capable of NA compression or reduction of the excitation fiber output, which is simple to manufacture, and which effectively reduces the NA between the input end of the fiber and the output end.

SUMMARY OF THE INVENTION

It is an object of this invention to provide an improved optical fiber with Numerical Aperture compression.

It is another object of this invention to provide an improved illumination optical fiber with Numerical Aperture compression using an outwardly flared conical taper at the output end of the fiber.

It is another object of this invention to provide an improved Numerical Aperture compression device which tends to collimate the light exiting an optical fiber.

It is a further object of this invention to provide an improved optical fiber with Numerical Aperture compression in which the output end of an excitation fiber has an outwardly-flared, uniform conical taper on it with a length substantially greater than the diameter of the widest portion of the taper.

In accordance with a preferred embodiment of the invention, an optical fiber with Numerical Aperture compression is comprised of a tapered fiber section. The tapered fiber section has a pre-established length, with an input end having a first predetermined diameter and an output end of a second predetermined diameter, greater than the first predetermined diameter.

BRIEF DESCRIPTION OF THE DRAWINGS

FIGS. 12 and 3 are cross-sectional side views and end views, respectively, of a variation of the embodiment of the invention shown in FIG. 12.

DETAILED DESCRIPTION

Figure 1:
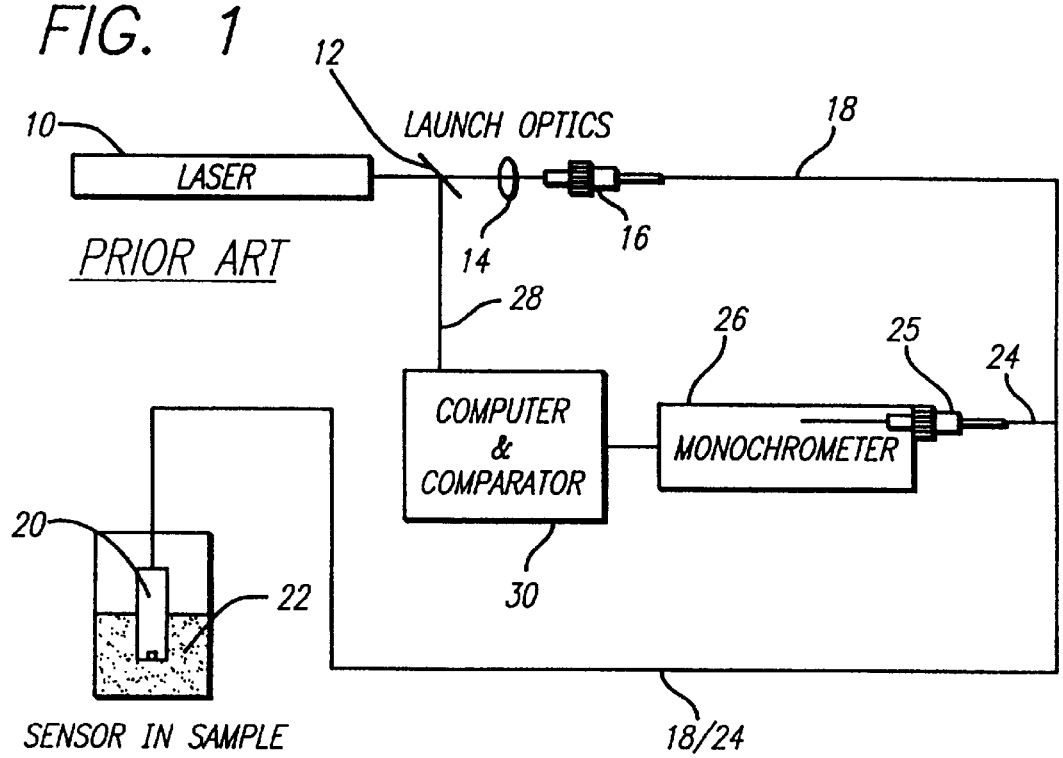
FIG. 1 is a diagrammatic representation of a spectroscopy system using fiber optic components.

Reference now should be made to the drawings, in which the same reference numbers are used throughout the different figures to designate the same components. FIG. 1 is a diagrammatic representation of a typical light-scattering spectroscopy probe system using a bifurcated fiber probe of the type illustrated in FIG. 2. Systems of this type are employed in various types of spectroscopy, such as absorption/transmission spectroscopy, fluorescence spectroscopy and light scattering spectroscopy. An optical source, such as a laser 10, supplies a beam of light to a beam splitter 12, with a portion of the light beam then being applied through a focusing lens 14 to the end of a fiber optic coupler 16. The coupler 16 is connected to the input end of an optical fiber 18, which preferably is a silica-clad silica core (si/si) fiber. Although other optical fibers are available, such as polymer-clad silica fibers (PCS), such fibers typically have an unacceptably high intrinsic fluorescence which precludes their use in light-scattering spectroscopy probes. The excitation energy carried by the fiber 18 is supplied to a probe 20, which is immersed in a sample 22. Often, the probe 20 is provided with a mirrored cap to space a mirror a pre-established distance from the end of the optical fiber 18. Such caps (not shown in FIG. 1) have apertures in them to allow the fluid of the sample 22 to pass into the cap; so that the energy exiting the end of the optical fiber 18 is reflected back from the mirror. A single fiber may be used in the system of FIG. 1 to also conduct reflected energy from the end cap or other reflective surface in the sample 22 into a collection fiber 24 (shown in FIG. 1 as common with the excitation or illumination fiber 18). The reflected energy or scattered fluorescence then is applied back to an optical splitter and into a coupler 25 connected to a monochrometer 26. The output of the monochrometer 26 is supplied to a computer and comparator 30, as one of two inputs. The other input to the comparator 30 is supplied from the beam splitter 12 through an optical fiber 28. Comparison of the energy launched by the laser 10 as applied to the computer and comparator 30 by way of the optical fiber 28, with the reflected energy supplied through the monochrometer 26 then permits the desired spectroscopic analysis.

Figure 2:
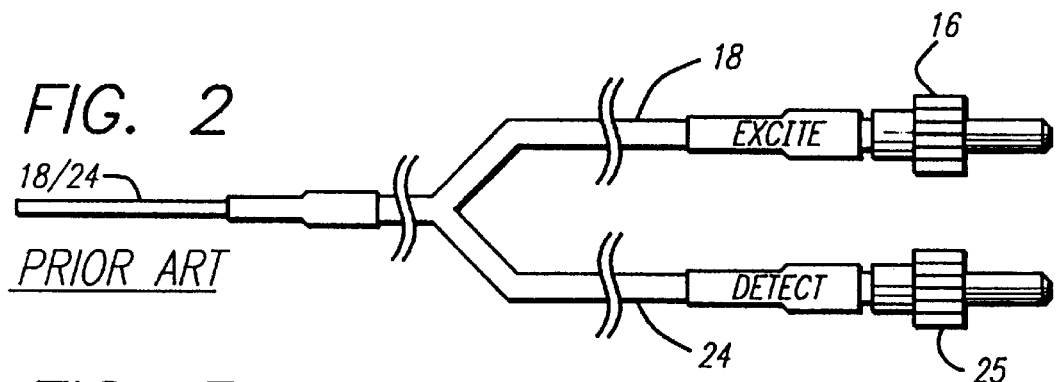
FIG. 2 is a representation of a typical fiber optic probe of the type used in the system shown in FIG. 1.

Systems of the type shown in FIG. 1 typically use a bifurcated probe of the type shown in FIG. 2, which illustrates in greater detail the different components of the portion of the system shown in FIG. 2 at the point where the excitation or illumination fiber 18 and the collection or detection fiber 24 separate. The system of FIGS. 1 and 2 is very inefficient. Generally, in fluorescence spectroscopy, the low Numerical Aperture (NA) of si/si fiber and the solid sphere emission of fluorescence from the sample 22 are incompatible. A very small portion of the emitted light is collected for transmission to the monochrometer 26. In addition, as the probe-to-target distance is increased, the divergence of the excitation radiation (12.7° half-angle for common 0.22 NA fiber) is high enough that energy density sufficient to stimulate fluorescence rapidly drops away. Additional complications also can arise in probes of the type depicted in FIGS. 1 and 2 in that contamination and damage to the fiber assembly is possible, due to the direct contact of the fibers with the analyte.

Figure 3:
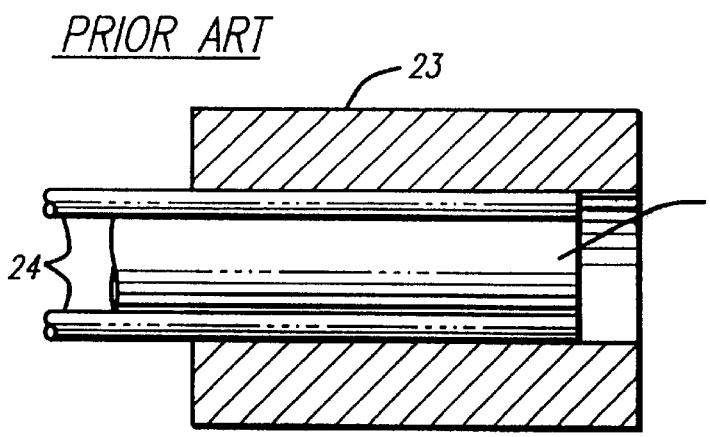
FIGS. 3 and 4 are cross-sectional side views and cross-sectional end views, respectively, of prior art devices used in the systems and probe of FIG. 2.
Figure 4:
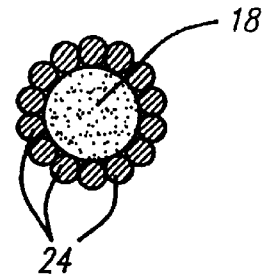

In an effort to improve the performance of the system shown in FIGS. 1 and 2, prior art systems have been designed as illustrated in FIGS. 3 and 4, with a separate excitation fiber 18 and a number of collection fibers 24 located in a ring or circle around the exterior of the collection fiber 18. Typically, these fibers are housed in a steel tube 23. As shown in FIG. 3, the excitation fiber 18 and the collection fibers 24 may be set back from the end of the tube 23. The space which is shown in FIG. 3 then may be filled with a suitable optical plug (or quartz window) to prevent contamination from the sample 22 on the ends of the excitation optical fiber 18 and the ends of the collection fibers 24. The bundle of FIGS. 3 and 4 is utilized in the sample of the spectroscopy system of FIG. 1 in the same manner described previously. While the device of FIG. 3 does exhibit an improved ability to collect more of the scattered light, due to numerous fibers for collection surrounding the central excitation fiber, it is still highly inefficient because the NA of the fibers used is incompatible with the efficient delivery of excitation energy and collection of highly scattered fluorescence.

To provide the most minimally invasive, highest flexibility, lowest cost or smallest sample requirement, fibers 18 and 24 are desired to be of small diameter. NA is a measure of the ability of an optical fiber to gather light where NA=sin θ, where θ is the maximum off-axis angle of light incident upon a fiber face that will be taken up by the fiber. While high NA fibers are desirable for collection of the available light from a source, such as the laser 10, such high NA fibers also produce a wider angle of divergence or scattering at the output end. Thus, the target, either with a surgical probe or a spectrographic probe of the type described in conjunction with the system of FIG. 1, must be quite close to the end of the fiber to achieve the energy densities desired.

In the past, it had been considered that one way to gather the maximum amount of light available from a laser source 10 into a fiber was to provide a light funnel; so that large focal spots could be forced into a small diameter fiber. This appeared logical from considerations of water flow. While water can be channeled through a small hole by way of a funnel, the rate of flow of the water is greatly reduced. Similar terms have been used in optics design, namely "fast" and "slow" to describe the acceptance of light into a fiber, "fast" being high NA and "slow" being low NA. While the expectation was that through the use of a tapered fiber, large focal spots could be forced into smaller diameter fibers, tapers were empirically found to be slow; they did not behave as light funnels. Lenses such as the lens 14 have been used to reduce the launch diameter; but such lenses increase the maximum launch angle of the laser light and, consequently, increase the NA of fiber required to gather that light.

Figure 5:
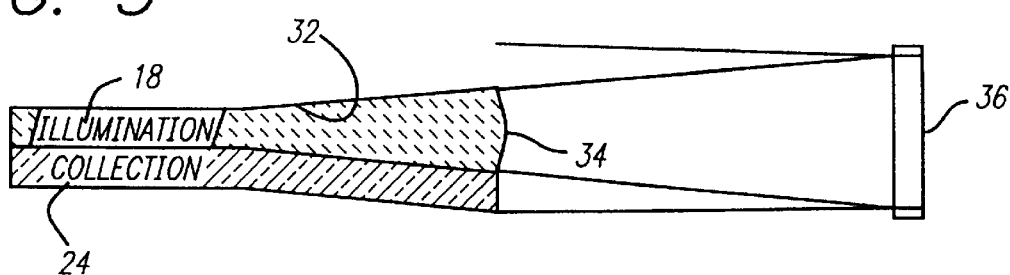
FIG. 5 is a cross-sectional representation of a preferred embodiment of the invention which is to be substituted for the prior art devices of FIGS. 3 and 4.
Figure 6:
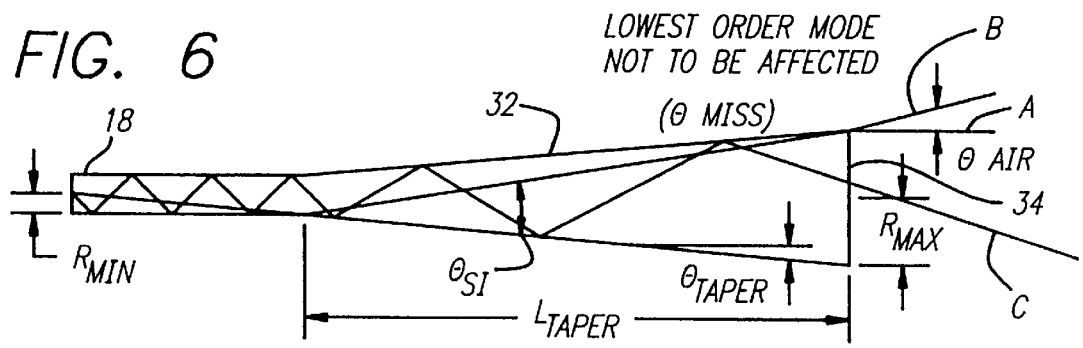
FIG. 6 is a diagrammatic representation of reflected light rays of the embodiment shown in FIG. 5.

Reference now should be made to FIGS. 5 and 6, which illustrate in diagrammatic form, a preferred embodiment of the invention. Ideally, for both surgical applications and for spectroscopy applications, fiber of relatively small diameter typically is desired for compatibility with the detector input. This is particularly true for surgical applications where relatively high flexibility of the fiber is important. As mentioned previously, however, such high NA fibers typically require the probe end or working end to be very close to the target. This is difficult and can lead to operating device failures, in surgical applications in particular. In an effort to overcome the conflicting requirements of a high NA input and a low NA output, the device of FIG. 5 has been designed. The illumination fiber 18 has an output section in the form of a tapered conical fiber section having an elongated taper 32. This section has a uniform taper angle along its entire length, terminating at a face 34, which may be either flat or in the form of a spherical or aspherical lens of small radius, as indicated in FIG. 5.

In the example shown in FIG. 5, a reflective surface, in the form of a mirror 36, is provided. This surface 36 is of the type which would be used in a spectroscopy application of the type shown generally in the system of FIG. 1. The mirror 36 reflects light back to a collection fiber 24, which, in the illustration of FIG. 5, has a uniform diameter throughout its length. As illustrated in FIG. 5, the fibers 18 and 24, along with the tapered section 32, are in physical contact with one another, and preferably are fused together.

For a high NA input fiber 18, having for example an NA of 0.22 NA, an elongated taper 32 of approximately 16 mm in length on a 300 $\mu$M core causes a 0.22 NA input fiber to have an output divergence equivalent to a 0.055 NA fiber. This is especially important in absorption spectroscopy, because a high NA, broad-spectrum source is required. A high NA fiber is required to couple as much light as possible into the fiber; but the high NA is a problem when a large fixed sample path is required to be traversed, as discussed above. If a high NA output is present, the illumination light becomes too weak for gathering information at even modest path lengths (1 to 2 centimeters). For example, in the illustration shown in FIG. 5, the distance from the end of the collection fiber to the mirror 36 is one centimeter, providing an overall path length of 2 centimeters.

By utilizing the structure illustrated in FIG. 5, with a 3:1 taper in the tapered section 32, a ten-fold gain in efficiency is obtained from the four-fold reduction or compression in the NA which takes place in the tapered section 32. Similar significant improvements are obtained in light scattering spectroscopy applications through enhanced quantum yields and other effects.

FIG. 6 illustrates some typical light rays and the modifications which take place with these rays as they undergo the NA shifting effect in the tapered section 32 of the device shown in FIG. 5. Each contact (bounce) a ray has with the tapered wall shifts the ray to a lower angle (NA) by $2\theta_{taper}$. It should be noted that a short, high ratio taper (large angle $\theta$) will shift high order modes by more (per bounce) than long low angle tapers; but the maximum NA shift is limited to the highest order mode that will never hit the wall of the taper, i.e., the mode with propagation angle equal to $\theta_{taper}$. In order to maximize the NA shift or compression, low angle tapers are desired where the low order modes make multiple bounces and the highest order mode that misses the taper wall is equal to the taper angle $\theta_{taper}$. This is the highest order mode desired in the NA reduction.

The minimum radius $r_{min}$ is shown at the input end of the optical fiber 18. While the length of the section of fiber 18 shown in FIG. 6 is quite short, it is to be understood that this length of fiber typically is substantially greater in length than the length of the tapered section 32. For purposes of illustration, however, only a short section of the fiber 18 is shown in FIGS. 5 and 6. The tapered section 32 then has a length $L_{taper}$ which extends from the output end of the section 18 to the end of the taper 34. It should be noted that the taper section 32 is an integral part of the fiber 18. No gap or fusion splice is required, though fusion may be used in some embodiments.

Two rays are traced as passing through the assembly shown in FIG. 6. Waveform "B" is the highest order mode which is not affected by the taper (this ray does not bounce against any of the taper walls). As indicated in FIG. 6, this ray receives its final internal reflection at the end of the fiber section 18, and exits from the taper end 34 precisely at the upper edge at the face 34. When the ray exits into the air, it undergoes a further slight upward bend at the angle of $\theta$ due to refraction; and the angle $\theta_{miss}$ of the waveform B is the highest order mode which is not affected by the structure, since this ray undergoes no reflections within the taper 32. Examination of waveform "C" illustrates the manner in which the taper 32 tends to flatten or reduce the NA of light rays passing through the composite assembly. As is readily apparent from an examination of the left-hand portion of FIG. 6, the ray C undergoes multiple relatively high-angle bounces within the section 18. As this ray enters the taper 32, the bounces are at much wider and flatter angles, increasing with each bounce; so that the exit angle of the ray at the surface 34 is nearer the axis of the composite assembly consisting of the input fiber 18 and the tapered section 32. It should be noted that no light ray can make too many bounces, shifting the angle through $\theta$ and back to higher angles.

It should be noted that when calculating the highest mode angle for a given fiber, it is best to choose the maximum NA within the fiber manufacturer's published tolerance. A ray which comes from a bounce on the wall of the opposing fiber just before entering the taper (ray "B") and exiting at the edge of the taper is the highest order that will miss. As such, this worst case ray could be used to define the minimum taper length. The other extreme case is the highest order mode, also making its last standard bounce just at the opening of the taper, such that the first bounce it makes is well within the tapered section. If calculations reveal this ray will make sufficient bounces, N, such that the original highest order mode angle less $2N\theta$ is equal or less than the highest order mode that will not make a bounce or ray $\theta_{miss}$:

$\theta_{max} - 2N\theta \leq \theta_{miss}$ where $\theta_{miss}$ is the highest order not affected by the taper, $\theta_{max}$ is the highest order mode in the fiber core, and $\theta_{taper}$ is the one-half angle of the taper. An optimum design exists where the NA shifted highest order mode C is equal to the highest order unaffected B at the fiber output. The taper angle and the maximum angle that misses a bounce are only equal for a taper of infinite length.

For a fiber 18 and taper 32 made of synthetic fused silica, the refractive index is about 1.447 in the near infrared (IR) to about 1.561 in the deep ultraviolet (UV). The refractive index of air is taken as 1 (though this is not strictly correct); and there also is a temperature dependence for the refractive index of silica that varies with wavelength; although it is quite small.

An ideal technique for forming the tapered section 32 is to form it integrally with the exit end of the illumination fiber 18. This is accomplished by an "up-taper" formation in which the raw material is fed into a melt zone. The fiber is rotated in a laser beam to uniformly heat the circumference; and the fiber is mechanically moved to remove earlier work from the interaction zone with the laser beam. The technique employs surface tension to drive the taper formation upward, and the freezing or solidifying of the glass is accomplished through application of varying amounts of heat energy. By controlling the heat and the rate at which the raw material fiber is fed from below, the fiber diameter increases in a non-linear rate, in that growth requires more fiber in each frame or time interval as the taper is formed to yield a linear taper angle. Once the final taper size and length has been obtained, it is cut at its maximum diameter to form the end 34 to eliminate a "tear drop" shape and leave a simple conical taper 32. In fluorine-doped silica-clad silica-core fiber, the cladding is conserved throughout the procedure; although some material is lost to vaporization in the larger portions of the taper. The energy is applied by way of a cylindrical lens, such that a line of energy rather than a spot, is focused on the fiber. This serves to average any fluctuation in energy and motion, so that the taper walls are as smooth as possible. Other techniques for building glass fiber tapers may be used, such as mechanical or laser machining from rod stock or formation in a controlled furnace. Ideally, the tapers should be of a uniform angle throughout its length, with smooth uniform side walls to provide optimum light reflection to accomplish the NA compression desired.

What is accomplished by the tapered output of the device shown in FIGS. 5 and 6 is an increase in the collimation of light exiting from the surface 34 of the tapered section. If, as illustrated in FIG. 5, the end of the taper 34 also is provided with a spherical or near spherical lens surface, further focusing of the output light from the end 34 is accomplished. Thus, that a close approximation of collimated light is obtained and directed to the mirror 36 (for absorption spectroscopy application) or toward the target (for a surgical probe or fluorescence spectroscopy application).

In the construction of an output taper of the type shown in the device 18/32 of FIG. 5, tapers with a 3:1 ratio and 16 mm long on a 300 μm core fiber have been produced. High NA laser energy was launched into these fibers; and the output spot diameters were measured at a fixed distance of 80 mm from the fiber faces. The standard fiber (without a taper) gave a spot of approximately 40 mm diameter, while a tapered output fiber gave a spot diameter of just under 11 mm. Calculating the NA of these outputs gave 0.24 for the standard fiber (published NA is 0.22±0.02) and 0.06 for the tapered output. This is a four-fold reduction or compression in NA.

Figure 7:
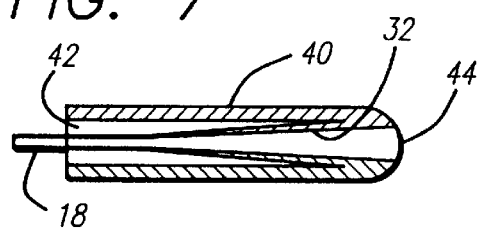
FIG. 7 is a cross-sectional view of a surgical probe incorporating the preferred embodiment of the invention shown in FIG. 5.

For surgical applications, such as coagulation of tissue in a gastro-intestinal medical application, the assembly shown in FIG. 7 may be constructed. As illustrated in FIG. 7, the input optical fiber 18 is integrally connected physically and optically with a tapered section 32. This section 32 is encased in a fused quartz ferrule 40; and the end of the tapered section 32 is integrally formed with a lens surface 44, or has a lens surface 44 added to it. The combination of the lens surface 44 and the operation of the taper 32 serves to produce a nearly collimated (low NA) output. For a hypothetical coagulation procedure, if a 2 mm or smaller spot is required to generate the desired effect, the 3:1 up-taper on 300 μm core fiber previously described may be held as far as 10 mm from the target tissue as opposed to a maximum of 3.8 mm for a standard 300 μm core fiber. Thus, the probe of FIG. 7 is ideal.

Figure 8:
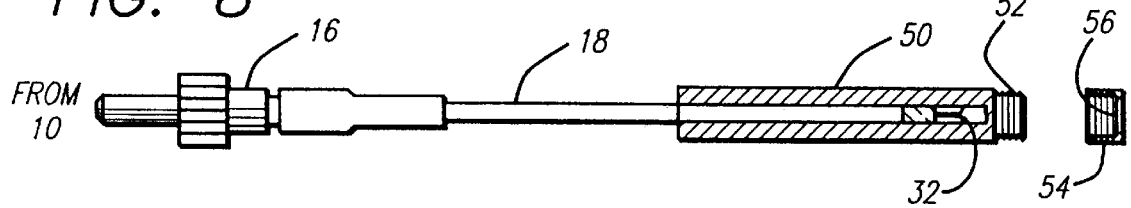
FIGS. 8 and 9 are partial cross-sectional side views of absorption spectroscopy probes using the preferred embodiment of the invention shown in FIG. 5.

FIG. 8 is a diagrammatic representation in partial cross section of an absorption/transmission spectroscopy probe utilizing a single-taper construction as illustrated in FIG. 5 for the parts 18, 32 and 34. The single fiber construction shown in FIG. 9 employs a steel or polymer housing 50 about the taper 32, which may be contained within a quartz ferrule 40 of the type shown in FIG. 7. The end of the housing 50 then is externally threaded at 52 to permit a threaded cap 54 to fit over the end. The internal end surface of the cap 54 is a mirrored surface 56, which then is located at one-half of the desired path length for the spectroscopy which is to be effected by the device. The cap 52 and/or the end of the housing 50/52 beyond the end of the up-tapered section 32 is provided with apertures to permit the sample to fill the space between the end of the taper 32 and the mirror 56.

Figure 9:
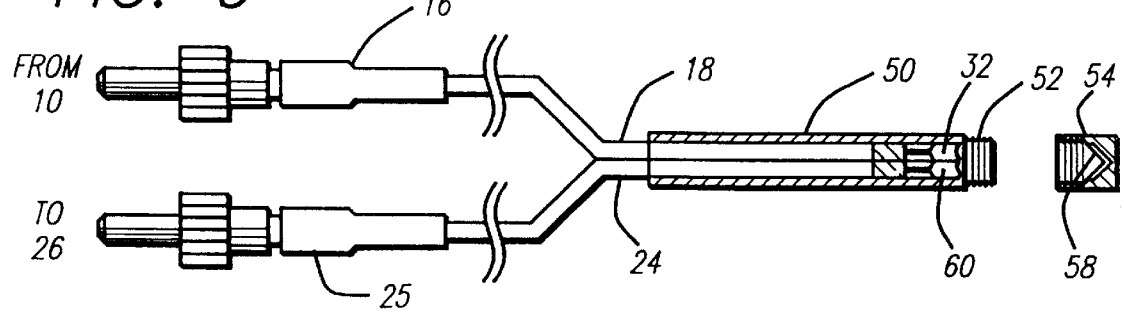
Figure 11:
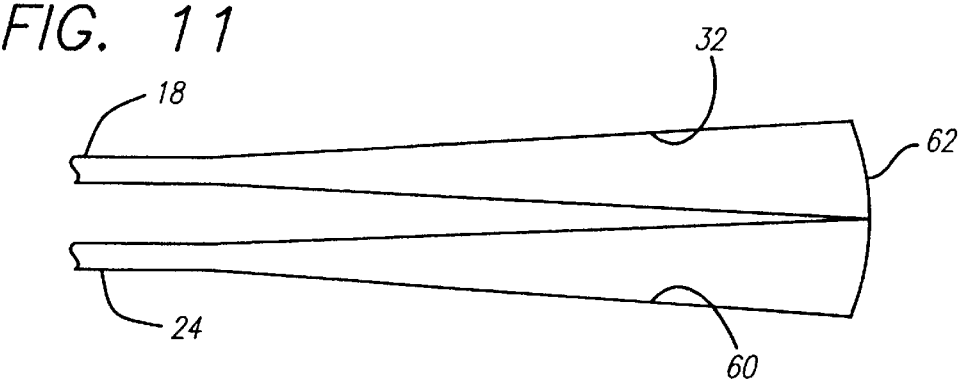
FIG. 11 is a diagrammatic representation of a variation of the invention shown in FIG. 5.

FIG. 9 illustrates a dual fiber probe which is similar to the probe of FIG. 8. In the probe of FIG. 9, the same reference numbers which are used in FIG. 1 also are employed for similar components of the device of FIG. 9. Once again, the two fibers may be encased in a housing 50 with the end of the taper 52 and the collection end of the collection fiber 60 located adjacent one another as illustrated in FIG. 11. A cap 54 having a pair of mirrors or a prism in it then is employed for reflecting the spot of light emitted by the tapered section 32 back to the end of the collection fiber 60 for utilization in the spectrometer. The advantages of the NA reduction or compression are inherent in this construction; and the same principles which have been described above apply in the reverse for the tapered collection fiber. The increased collection surface area provided by the tapered collection fiber improves the probe efficiency by several orders of magnitude while matching the NA of the reflected light perfectly.

Figure 10:
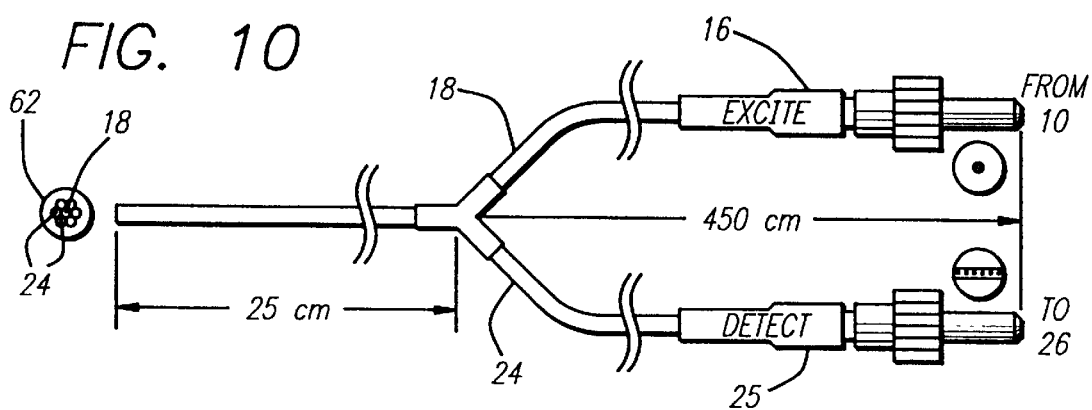
FIG. 10 is a variation of the probe shown in FIG. 2 used to incorporate structures of the preferred embodiment of the invention shown in FIGS. 5 and 6.

FIG. 10 is a variation of a probe of the type shown in FIG. 9, but which employs a plurality of collecting fibers 24 surrounding a central excitation or illumination fiber 18. All of these fibers can terminate in a probe of the type shown in FIG. 9; and the excitation fiber 18 preferably terminates in an up-tapered section 32 of the type shown in FIG. 5. The ring of collection fibers may be simple, straight or taper ended fibers. The orientation of the fibers at the input ends and at the output ends are illustrated in the diagrammatic circles located at the right-hand end and the left-hand end of the multiple fiber probe shown in FIG. 10.

FIG. 11 is a diagrammatic representation of a variation of the device shown in FIG. 5, in which the illumination fiber combination including the optical fiber 18 and the up-tapered section 32 terminate in a common face 62, with the input of a down-tapered collection fiber combination including a tapered section 60 and the collection fiber 24, of the type illustrated in FIG. 9, for example. As illustrated in FIG. 11, a common lens surface 62 is provided to cause overlap of the light exiting from the up-tapered section 32 and the insertion cone of the down-tapered section 60 of the collection fiber 24. With sufficient NA compression or reduction effected by the tapered section 32, a lens such as the lens 62 may not be necessary; but the lens does improve the amount of overlap which takes place. By employing the down-tapered section 60 on the collection fiber 24, improved collection of the available reflected light when the device of FIG. 11 is used in various types of spectrographic systems is achieved over the prior art devices which are shown and described above in conjunction with FIGS. 3 and 4.

Figure 12:
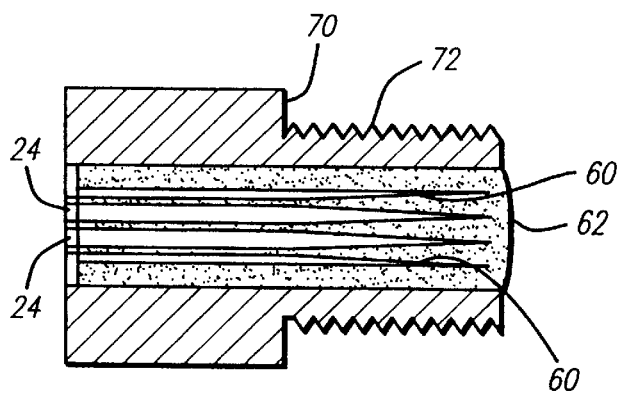
Figure 13:
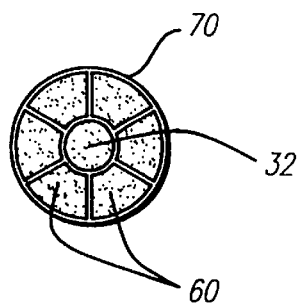

FIGS. 12 and 13 comprise a side cross-sectional view and an end view, respectively, of a modification of the prior art device of FIGS. 3 and 4, which incorporates applicant's preferred embodiment of the invention. A central illumination fiber terminates in an up-tapered section 32, which is shown most clearly in the end view of FIG. 13. This section is surrounded by a plurality of down-tapered sections 60, which are coupled to corresponding collection fibers 24. The entire assembly is housed within a quartz ferrule 70, which has a threaded external portion 72 on it. As illustrated in FIG. 12, a lens 62 of the type shown in FIG. 11 is placed or formed on the device. The desirable effects of surrounding the illumination or excitation taper 32 with a plurality of tapered collection fibers 60 results in improved operating characteristics over the device of FIGS. 3 and 4. The fiber array using multiple (six as shown in FIG. 13) collection fibers represents what may be considered to be an ultimate design for use in many spectroscopy applications.

The advantages which are obtained with the devices of FIGS. 5 through 13 are particularly significant, for example, when the surgical probe of FIG. 7 is considered. In surgical applications using a single fiber, the reduced divergence of the output which is obtained from the use of the up-tapered (NA reduction) conical section 32 permits maintenance of minimum therapeutic energy densities at considerably larger separation distances than was possible with prior art devices. For example, in free-beam (normal flat polish on unmodified optical fiber) surgical fibers, 0.22 NA and 300 $\mu$m core diameter, if the surgeon must maintain a spot of 3 mm diameter to obtain therapeutic effectiveness but cannot drop below 2 mm diameter or the tissue chars and damages the fiber, the fiber tip must be maintained between 1.6 and 6 mm from the tissue. While this does not seem too difficult on initial examination, in reality if the fiber is held near the close limit of the tissue, spattering tissues (blood, fat, connective tissue) quickly cover the fiber output and burn. Damage to the fiber then results. For a 3:1 NA reduction taper on the same fiber, the operational separation distance becomes 1 mm to 19 mm. This is huge by comparison with the distance which could be tolerated with the prior art device.

In addition, for illumination applications in medicine (including UV curing of dental adhesives), single fiber tapers such as the one shown in FIG. 7, can serve to deliver more intense spots of light through endoscopes without the additional diameter requirements of conventional lens systems.

The foregoing description of the preferred embodiment of the invention should be taken as illustrative, and not as limiting. Various changes will occur to those skilled in the art for performing substantially the same function, in substantially the same way, to achieve substantially the same result, without departing from the true scope of the invention as defined in the appended claims.

What is claimed is:

1. An optical fiber with Numerical Aperture (NA) compression comprising:
   a tapered fiber section of a predetermined length having a light input end of a first predetermined diameter and having a light output end of a second predetermined diameter greater than said first predetermined diameter, said tapered fiber section further being encased in a ferrule, and said light output end is either integrally formed with a lens surface or has a lens surface added thereto.

2. The combination according to claim 1 wherein said tapered fiber section has a uniform taper from the light input end thereof to the light output end thereof.

3. The combination according to claim 2 wherein said tapered fiber section has a generally conical shape.

4. The combination according to claim 1 wherein said tapered fiber section has a generally conical shape.

5. An optical fiber with Numerical Aperture (NA) compression including in combination:
   a first fiber section having a light input end and a light output end and having a first predetermined diameter;
   a tapered fiber section of a predetermined length having an input end of said first predetermined diameter optically coupled with the output end of said first fiber section and having an output end of a second predetermined diameter greater than said first predetermined diameter,
   a ferrule that is large enough to encase the tapered fiber section, and
   a lens surface that is optically coupled with the output end of the tapered fiber section.

6. The combination according to claim 5 wherein said tapered fiber section has a uniform taper from the light input end thereof to the light output end thereof.

7. The combination according to claim 6 wherein said tapered fiber section has a generally conical shape.

8. The combination according to claim 7 wherein said first end of said tapered fiber section is physically coupled with the output end of said first fiber section.

9. The combination according to claim 8 wherein said tapered fiber section is integrally formed with said first fiber section on the output end thereof.

10. The combination according to claim 9 wherein said first fiber section and said tapered fiber section comprise glass fibers.

11. The combination according to claim 10 wherein the taper of said tapered fiber section from the input end thereof to the output end thereof is at least 3:1.

12. The combination according to claim 11 further including a collimating lens on the output end of said tapered fiber section.

13. The combination according to claim 5 wherein said tapered fiber section has a uniform taper angle $\Theta$.

14. The combination according to claim 13 wherein said tapered fiber section has a generally conical shape.

15. The combination according to claim 5 wherein said first end of said tapered fiber section is physically coupled with the output end of said first fiber section.

16. The combination according to claim 15 wherein said first fiber section and said tapered fiber section comprise glass fibers.

17. The combination according to claim 16 wherein said tapered fiber section has a generally conical shape.

18. The combination according to claim 5 wherein said tapered fiber section is integrally formed with said first fiber section on the output end thereof.

19. The combination according to claim 5 wherein said tapered fiber section is integrally formed with said first fiber section on the output end thereof.

20. The combination according to claim 5 further including a collimating lens on the output end of said tapered fiber section.

21. The combination according to claim 5 wherein said first fiber section and said tapered fiber section comprise glass fibers.

22. An optical fiber assembly with Numerical Aperture (NA) compression including in combination:
   an illumination fiber section having a light input end and a light output end and having a first predetermined diameter;
   a first tapered fiber section having a predetermined length with an input end of said first predetermined diameter and optically coupled with the output end of said illumination fiber section, and having an output end having a second predetermined diameter greater than said first predetermined diameter; and a collection fiber section having a light input end and a light output end, said collection fiber section is physically located with the light input end thereof adjacent the light output of said tapered fiber section and optically coupled to the light output of said tapered fiber section by a reflective or scattering surface.

23. The combination according to claim 22 wherein said output end of said illumination fiber section is physically and optically coupled with the input end of said first tapered section.

24. The combination according to claim 22 wherein said collection fiber section is a second tapered fiber section, and the light output end of said second tapered fiber section has a second predetermined diameter, and the light input end of said second tapered fiber section has a third predetermined diameter greater than said second predetermined diameter.

25. The combination according to claim 24 wherein said illumination fiber section, said first tapered fiber section and said collection fiber section all comprise glass fiber material.

26. The combination according to claim 25 wherein said collection fiber section comprises a plurality of substantially identical collection fiber sections.

27. The combination according to claim 26 wherein said plurality of collection fiber sections are physically arranged with the light input ends thereof around said first tapered fiber section.

28. The combination according to claim 27 wherein the output of said first tapered fiber section and the input ends of said collection fiber sections are fused to one another.

29. The combination according to claim 28 wherein said output end of said illumination fiber section is physically and optically coupled with the input end of said first tapered section.

30. The combination according to claim 22 wherein said illumination fiber section, said first tapered fiber section and said collection fiber section all comprise glass fiber material.

31. The combination according to claim 22 wherein said collection fiber section comprises a plurality of substantially identical collection fiber sections.

32. The combination according to claim 31 wherein said plurality of collection fiber sections are physically arranged with the light input ends thereof around said first tapered fiber section.

33. The combination according to claim 32 wherein the output of said first tapered fiber section and the input ends of said collection fiber sections are fused to one another.

34. The combination according to claim 22 wherein said plurality of collection fiber sections are physically arranged with the light input ends thereof around said first tapered fiber section.

\* \* \* \* \*